(12) United States Patent
Rezach et al.

(10) Patent No.: US 11,627,998 B2
(45) Date of Patent: Apr. 18, 2023

(54) HEAD POSITION AND DRIVER COMBINATION INSTRUMENT

(71) Applicant: Warsaw Orthopedic, Inc., Warsaw, IN (US)

(72) Inventors: William A. Rezach, Covington, TN (US); Brian A. Butler, Atoka, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 238 days.

(21) Appl. No.: 17/118,694

(22) Filed: Dec. 11, 2020

(65) Prior Publication Data

US 2022/0183725 A1    Jun. 16, 2022

(51) Int. Cl.
    *A61B 17/70*    (2006.01)
    *A61B 90/00*    (2016.01)
    *A61B 17/00*    (2006.01)

(52) U.S. Cl.
    CPC .......... *A61B 17/7082* (2013.01); *A61B 90/03* (2016.02); *A61B 2017/00455* (2013.01); *A61B 2090/035* (2016.02)

(58) Field of Classification Search
    CPC ............ A61B 17/7082; A61B 17/7076; A61B 17/7077; B25G 1/04; B25G 1/043; B25B 23/0021; B25B 23/0007
    USPC ............................................. 81/177.2, 177.5
    See application file for complete search history.

(56) References Cited

U.S. PATENT DOCUMENTS

| | | |
|---|---|---|
| 6,415,693 B1 | 7/2002 | Simon et al. |
| 6,497,166 B1 | 12/2002 | Fleckenstein |
| 6,857,343 B1 | 2/2005 | Easterbrooks et al. |
| 7,226,453 B2 | 6/2007 | Chao et al. |
| 7,572,264 B2 | 8/2009 | Null et al. |
| 7,771,459 B2 | 8/2010 | von Oepen |
| 7,846,167 B2 | 12/2010 | Garcia et al. |
| 7,947,047 B2 | 5/2011 | Amal |
| 8,048,124 B2 | 11/2011 | Chin et al. |
| 8,100,916 B2 | 1/2012 | Kumar et al. |
| 8,231,635 B2 | 7/2012 | Sharifi-Mehr et al. |
| 8,262,670 B2 | 9/2012 | Laubert et al. |
| 8,343,165 B2 | 1/2013 | Berrevoets |
| 8,394,108 B2 | 3/2013 | McLean et al. |

(Continued)

FOREIGN PATENT DOCUMENTS

| | | | | |
|---|---|---|---|---|
| WO | WO-2010105174 A1 | * | 9/2010 | ......... A61B 17/7032 |
| WO | WO-2019134738 A1 | * | 7/2019 | ......... A61B 17/8875 |

*Primary Examiner* — Jan Christopher L Merene
*Assistant Examiner* — Allie D Cline
(74) *Attorney, Agent, or Firm* — Fox Rothschild LLP

(57) ABSTRACT

Systems, instruments, and methods for performing a medical procedure. The methods comprise: obtaining a surgical instrument that combines a head positioner and a driver into a single integrated part (the driver being at least partially inserted through an elongate aperture formed in the head positioner so as to extend from a proximal end of the head positioner to a distal end of the head positioner); using an actuable structure of the head positioner to limit an amount that the driver can linearly travel in a first direction within the elongate aperture formed in the head positioner; causing a screw to threadingly engage an object via rotation of the driver in at least a first direction around a central axis of the surgical instrument; and changing an orientation of a receiver via rotation of the head positioner about a portion of the driver.

17 Claims, 11 Drawing Sheets

(56) References Cited

U.S. PATENT DOCUMENTS

| | | |
|---|---|---|
| 8,459,155 B2 | 6/2013 | Canizares, Jr. et al. |
| 8,460,307 B2 | 6/2013 | Saidha et al. |
| 8,540,756 B2 | 9/2013 | Olsen et al. |
| 8,747,411 B2 | 6/2014 | Mitchell |
| 8,763,499 B2 | 7/2014 | Dahners |
| 8,784,431 B1 | 7/2014 | Harder et al. |
| 8,845,652 B2 | 9/2014 | Heinz |
| 8,882,775 B2 | 11/2014 | LaPosta et al. |
| 8,900,248 B2 | 12/2014 | Biyani |
| 8,932,303 B2 | 1/2015 | Bouliane |
| 8,945,193 B2 | 2/2015 | Kirschman |
| 8,951,264 B2 | 2/2015 | Saidha et al. |
| 8,992,587 B2 | 3/2015 | Kirschman |
| 8,998,921 B2 | 4/2015 | Sharifi-Mehr et al. |
| 9,113,976 B2 | 8/2015 | Yevmenenko et al. |
| 9,138,279 B2 | 9/2015 | Laposta et al. |
| 9,216,044 B2 | 12/2015 | Nuckley et al. |
| 9,265,540 B2 | 2/2016 | Kirschman |
| 9,295,500 B2 | 3/2016 | Marigowda |
| 9,387,025 B2 | 7/2016 | Santangelo et al. |
| 9,526,553 B2 | 12/2016 | Bess et al. |
| 9,572,605 B2 | 2/2017 | Shipp |
| 9,597,135 B1 | 3/2017 | Miller et al. |
| 9,642,654 B2 | 5/2017 | Reimels et al. |
| 9,649,139 B2 | 5/2017 | Sharifi-Mehr et al. |
| 9,687,285 B2 | 6/2017 | Robinson |
| 9,949,731 B2 | 4/2018 | Erramilli et al. |
| 9,968,384 B2 | 5/2018 | Fischer et al. |
| 10,105,165 B2 | 10/2018 | Biedermann et al. |
| 10,117,684 B2 | 11/2018 | Saidha et al. |
| 10,285,740 B2 | 5/2019 | May et al. |
| 10,349,986 B2 | 7/2019 | Wall et al. |
| 10,390,967 B2 | 8/2019 | Livorsi et al. |
| 10,426,535 B2 | 10/2019 | Zander et al. |
| 10,448,978 B2 | 10/2019 | Wall et al. |
| 10,463,404 B2 | 11/2019 | Wall et al. |
| 10,470,805 B2 | 11/2019 | Biedermann et al. |
| 10,568,668 B2 | 2/2020 | Biedermann et al. |
| 10,639,080 B2 | 5/2020 | Sharifi-Mehr et al. |
| 10,646,261 B2 | 5/2020 | Folger et al. |
| 10,653,457 B2 | 5/2020 | Erramilli et al. |
| 10,702,315 B2 | 7/2020 | Lindner |
| 10,702,316 B2 | 7/2020 | Heuer |
| 2002/0166421 A1 | 11/2002 | Bowerman |
| 2002/0169453 A1 | 11/2002 | Berger |
| 2006/0241600 A1 | 10/2006 | Ensign et al. |
| 2007/0122764 A1 | 5/2007 | Balfour et al. |
| 2008/0041196 A1 | 2/2008 | Companioni et al. |
| 2008/0071274 A1 | 3/2008 | Ensign |
| 2008/0147128 A1 | 6/2008 | Fritzinger |
| 2008/0200918 A1 | 8/2008 | Spitler et al. |
| 2008/0215099 A1 | 9/2008 | Balfour et al. |
| 2008/0269768 A1 | 10/2008 | Schwager et al. |
| 2009/0005787 A1 | 1/2009 | Crall et al. |
| 2009/0264895 A1 | 10/2009 | Gasperut et al. |
| 2011/0137320 A1 | 6/2011 | von Oepen |
| 2011/0270322 A1 | 11/2011 | Olsen et al. |
| 2011/0282398 A1 | 11/2011 | Overes et al. |
| 2012/0203288 A1 | 8/2012 | Lange et al. |
| 2013/0072984 A1 | 3/2013 | Robinson |
| 2013/0072986 A1 | 3/2013 | Robinson |
| 2014/0018816 A1 | 1/2014 | Fenn et al. |
| 2014/0066945 A1 | 3/2014 | Humphreys et al. |
| 2014/0288567 A1 | 9/2014 | Kroll |
| 2014/0324062 A1* | 10/2014 | Heuer ................ A61B 17/7082 606/104 |
| 2015/0201987 A1 | 7/2015 | Lemoine et al. |
| 2015/0250521 A1 | 9/2015 | Poker et al. |
| 2015/0374417 A1 | 12/2015 | Petit et al. |
| 2016/0296266 A1* | 10/2016 | Chandanson ...... A61B 17/8875 606/104 |
| 2018/0146990 A1 | 5/2018 | Manzanares et al. |
| 2018/0235684 A1 | 8/2018 | Hawkes et al. |
| 2018/0353224 A1 | 12/2018 | Kam et al. |
| 2019/0083147 A1* | 3/2019 | Hackathorn, II .. A61B 17/8625 606/86 A |
| 2019/0175193 A1 | 6/2019 | Fenn et al. |
| 2019/0254729 A1 | 8/2019 | Rohlfing et al. |
| 2019/0254730 A1 | 8/2019 | Rohlfing et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030009 A1* | 1/2020 | Folger ................ A61B 17/7082 606/86 A |
| 2020/0038064 A1 | 2/2020 | Stoklund et al. |
| 2020/0078056 A1 | 3/2020 | Biedermann et al. |
| 2020/0121397 A1 | 4/2020 | Elliott et al. |
| 2020/0121398 A1 | 4/2020 | Elliott et al. |
| 2020/0229849 A1 | 7/2020 | Biedermann et al. |
| 2020/0237412 A1 | 7/2020 | Erramilli et al. |
| 2020/0282530 A1* | 9/2020 | Sharifi-Mehr .......... B25B 15/04 81/32 |

* cited by examiner

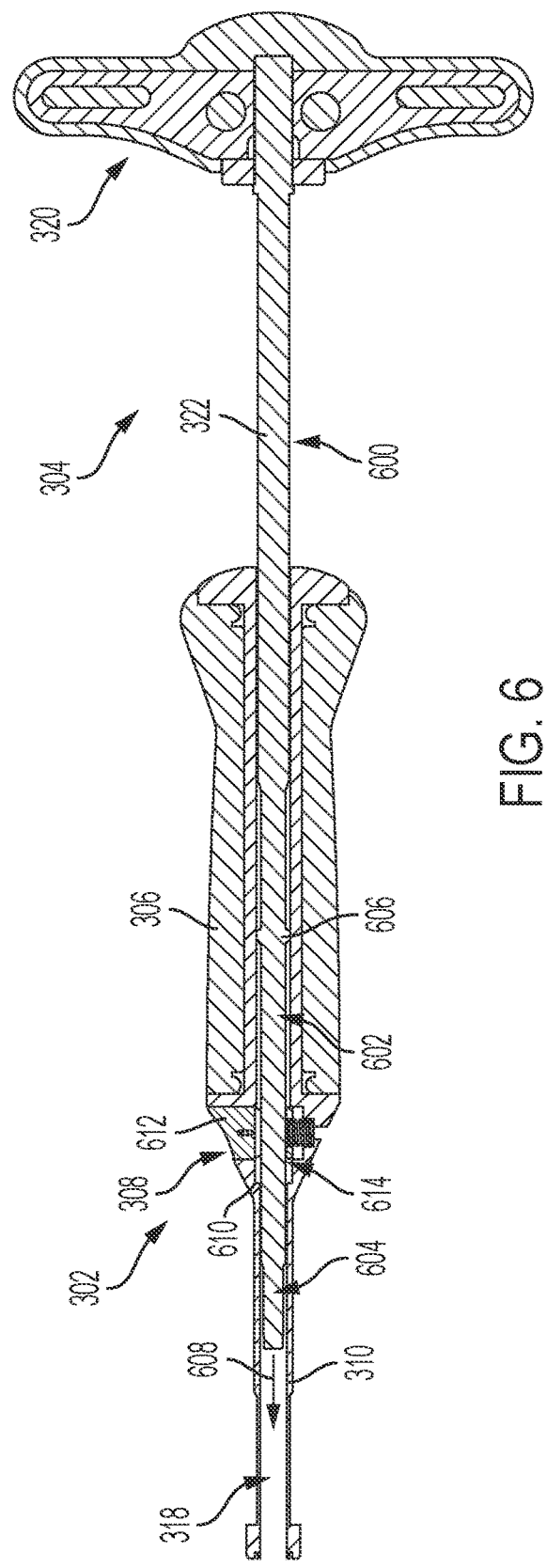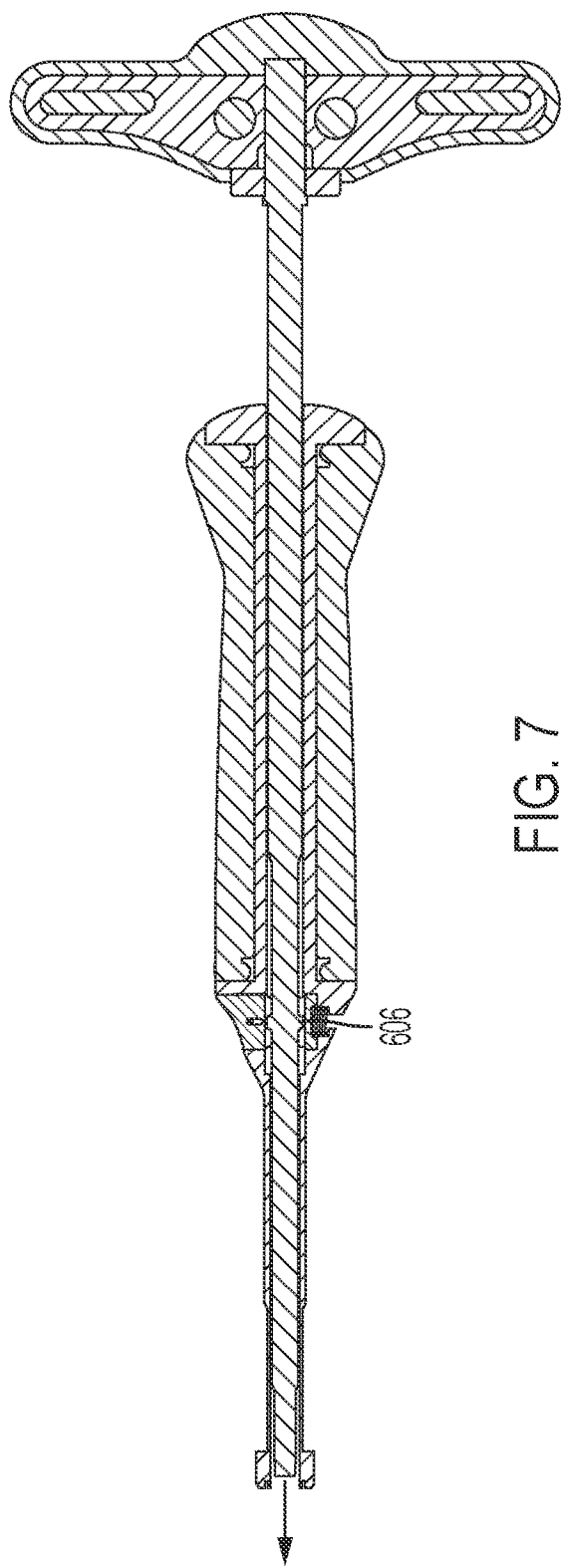
FIG. 6
FIG. 7

HEAD POSITION AND DRIVER COMBINATION INSTRUMENT

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to two or more vertebral members. This disclosure describes improvements over these prior technologies.

SUMMARY

The present disclosure relates to implementing systems and methods for performing a medical procedure. The methods may comprise: obtaining a surgical instrument that combines a head positioner and a driver into a single integrated tool (the driver being at least partially inserted through an elongate aperture formed in the head positioner so as to extend from a proximal end of the head positioner to a distal end of the head positioner); using an actuable structure (e.g., a button) of the head positioner to limit an amount that the driver can linearly travel in a first direction within the elongate aperture formed in the head positioner; causing a screw to threadingly engage an object via rotation of the driver in at least a first direction around a central axis of the surgical instrument; and changing an orientation of a receiver via rotation of the head positioner about a portion of the driver.

The methods may also comprise causing the screw to advance into the object by further rotating the driver in the first direction about the central axis of the surgical instrument. The actuable structure of the head positioner may be actuated (e.g., depressed) to stop limiting the amount that the driver can linearly travel in the first direction within the elongate aperture formed in the head positioner. When this occurs, the driver can be removed from the elongate aperture formed in the head positioner. Actuation of the actuable structure can be discontinued when the driver is at least partially removed from the elongate aperture formed in the head positioner.

In some scenarios, the actuable structure is resiliently biased by a resilient member into a first position in which the actuable structure at least partially obstructs the elongate aperture formed in the head positioner. The actuable structure can be actuated so that the resilient member no longer causes the actuable structure to obstruct the elongate aperture formed in the head positioner. The actuable structure can be released so that the resilient member once again causes the actuable structure to obstruct the elongate aperture formed in the head positioner. A surface of the elongate aperture may be used to limit an amount that the driver can linearly travel in a second direction within the elongate aperture formed in the head positioner.

The present document also concerns a surgical instrument. The surgical instrument may comprise a single integrated tool comprising both a head positioner and a driver. The driver is at least partially inserted through an elongate aperture formed in the head positioner so as to extend from a proximal end of the head positioner to a distal end of the head positioner. When the driver is fully inserted into the head position, a head of the driver extends through and projects out of a distal end of the head positioner.

The driver is configured to transfer torque to a screw. In this regard, the driver comprises, for example, a shank that (i) is linearly and rotationally movable within the elongate aperture of the head positioner, and (ii) has a distal end with a head sized and shaped to fit in a socket of the screw.

The head positioner is configured to engage a receiver for orientation adjustment. In this regard, the head positioner comprises, for example, an actuable structure (e.g., a button) that is configured to limit an amount that the driver can linearly travel in a first direction within the elongate aperture formed in the head positioner. Actuation of the actuable structure can cause the actuable structure to stop limiting the amount that the driver can linearly travel in the first direction within the elongate aperture of the head positioner. The driver is removable from the elongate aperture of the head positioner when the actuable structure is actuated.

In some scenarios, the actuable structure comprises a rigid member that is resiliently biased by a resilient member into a first position in which the rigid member at least partially obstructs the elongate aperture of the head positioner. The rigid member comprises a hole through which a shank of the driver passes when the driver is inserted into the head positioner. The rigid member engages a flange formed on a shank of the driver so as to limit the amount that the driver can linearly travel in the first direction within the elongate aperture of the head positioner. The resilient member no longer causes the actuable structure to obstruct the elongate aperture formed in the head positioner when the actuable structure is depressed. An internal shaped surface of the head positioner may limit an amount that the driver can linearly travel in a second direction within the elongate aperture of the head positioner.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 6 provides an illustration showing the driver in a first position relative to the inline handle.

FIG. 7 provides an illustration showing the driver in a second position relative to the inline handle.

DETAILED DESCRIPTION

Figure 1:
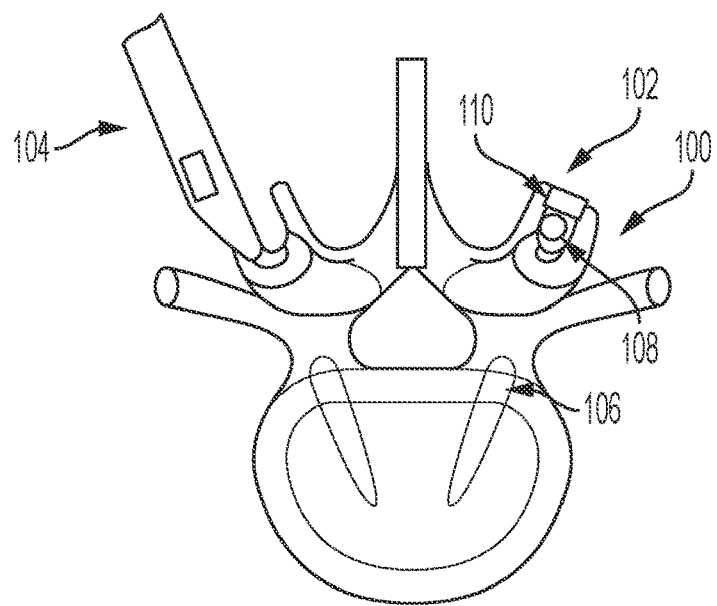
FIG. 1 is an illustration showing a surgical instrument being used to orient a receiver coupled to a spine.

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to medical devices and methods for treating musculoskeletal disorders, and more particularly, to surgical systems and methods for treating the spine. Embodiments of the devices, methods, and systems are described below with reference to the Figures.

Figure 2:
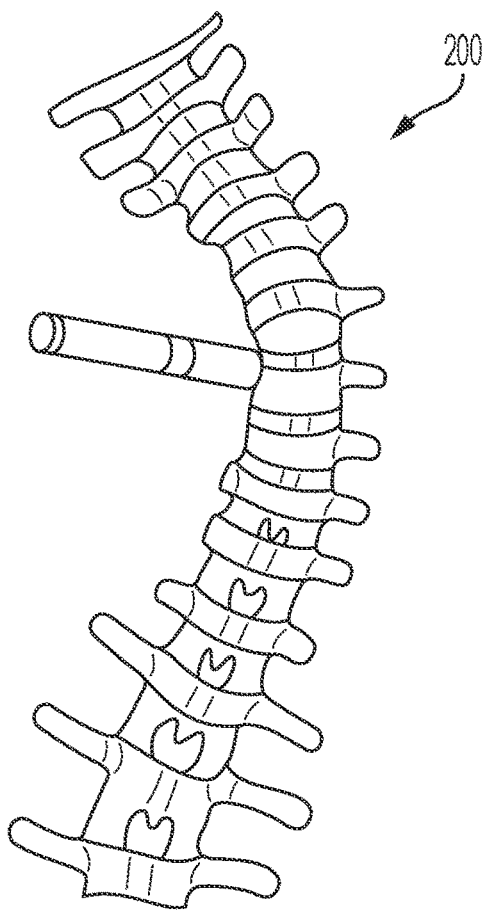
FIG. 2 is another illustration showing a plurality of receivers being oriented relative to each other and to a spine.

Referring now to FIGS. 1-2, there are provided illustrations that are useful for understanding an illustrative application in which the surgical instrument of the present solution can be employed. FIGS. 1-2 show a plurality of receivers 100 being properly oriented relative to each other and to a spine 200. Each receiver 100 is coupled to the spine 200 via a screw 106. Each receiver 100 comprises a u-shaped channel 102. A surgical instrument 104 is used to rotate a respective receiver 100 for aligning the u-shaped channel 102 with u-shaped channels of other receivers. Once the u-shaped channels are aligned, a rod 108 is disposed in all of the receivers of a given set, and secured therein. A set screw 110 is then inserted into a threaded aperture of the receiver 100, and caused to threadingly engage threads of the receiver for securely coupling the rod 108 to the receiver. The receivers, screws and rods are well known.

Conventionally, a plurality of surgical instruments are required for (i) driving the screw into bone of the spine 200, (ii) properly orienting the receivers, and (iii) driving the set screw into the receiver 100. This results in a relatively cumbersome and inefficient medical procedure. Accordingly, the present solution provides a novel surgical instrument that combines both a head positioner and a driver. The particulars of the novel surgical instrument will become evident as the discussion progresses.

Figure 3:
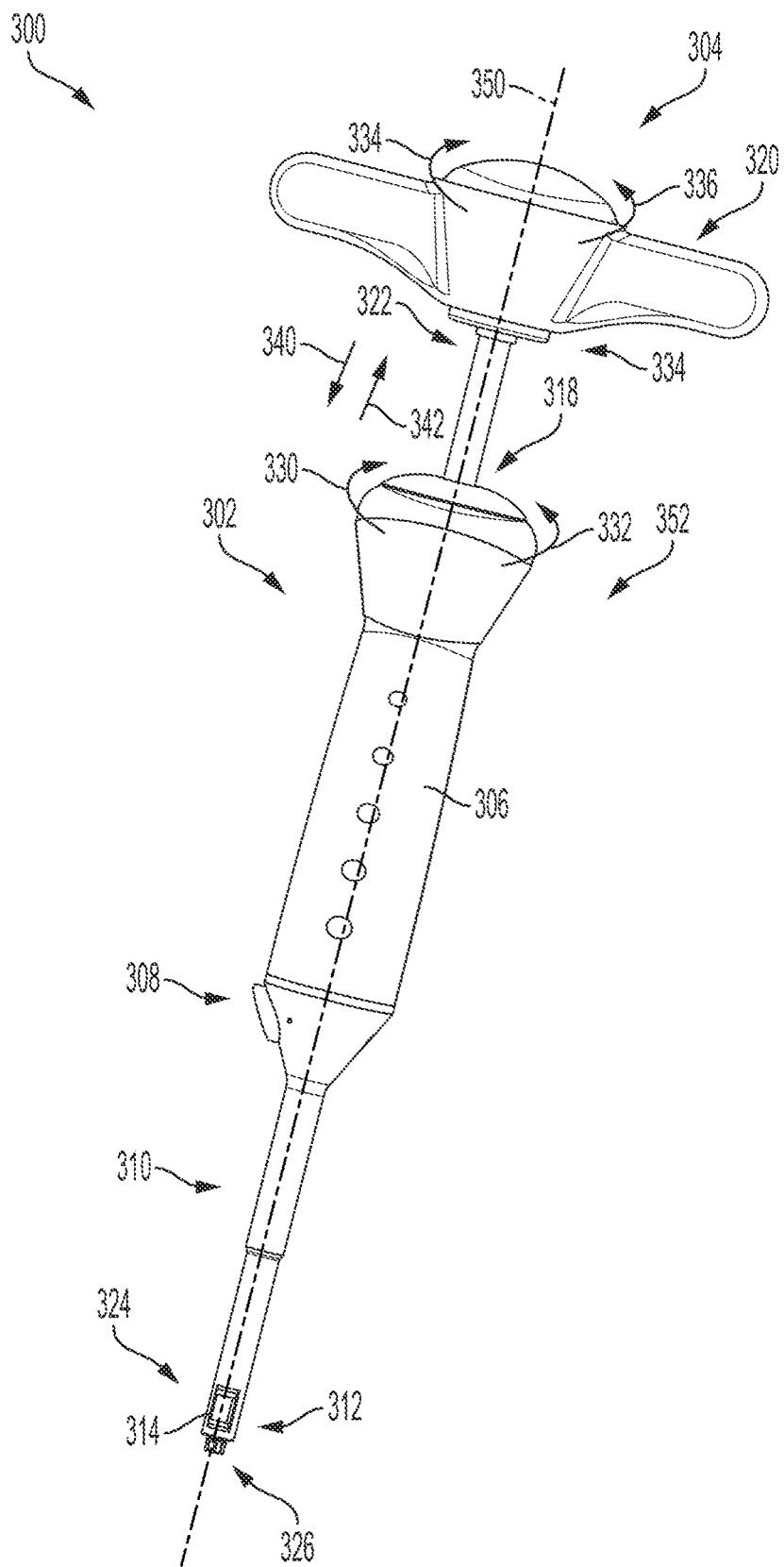
FIG. 3 is a perspective view of a surgical instrument that combines a head positioner and screw driver.
Figure 4:
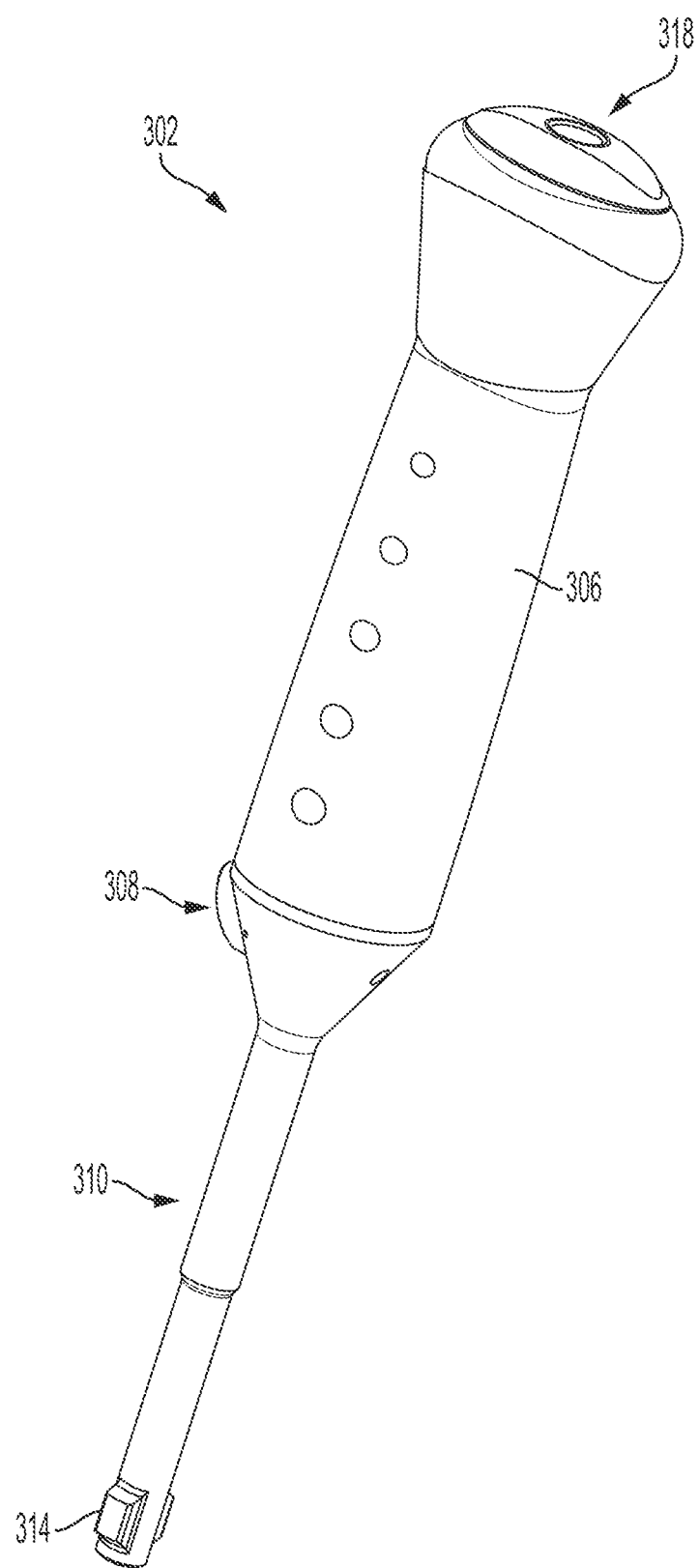
FIG. 4 is a perspective view of an inline handle of the surgical instrument shown in FIG. 3.
Figure 5:
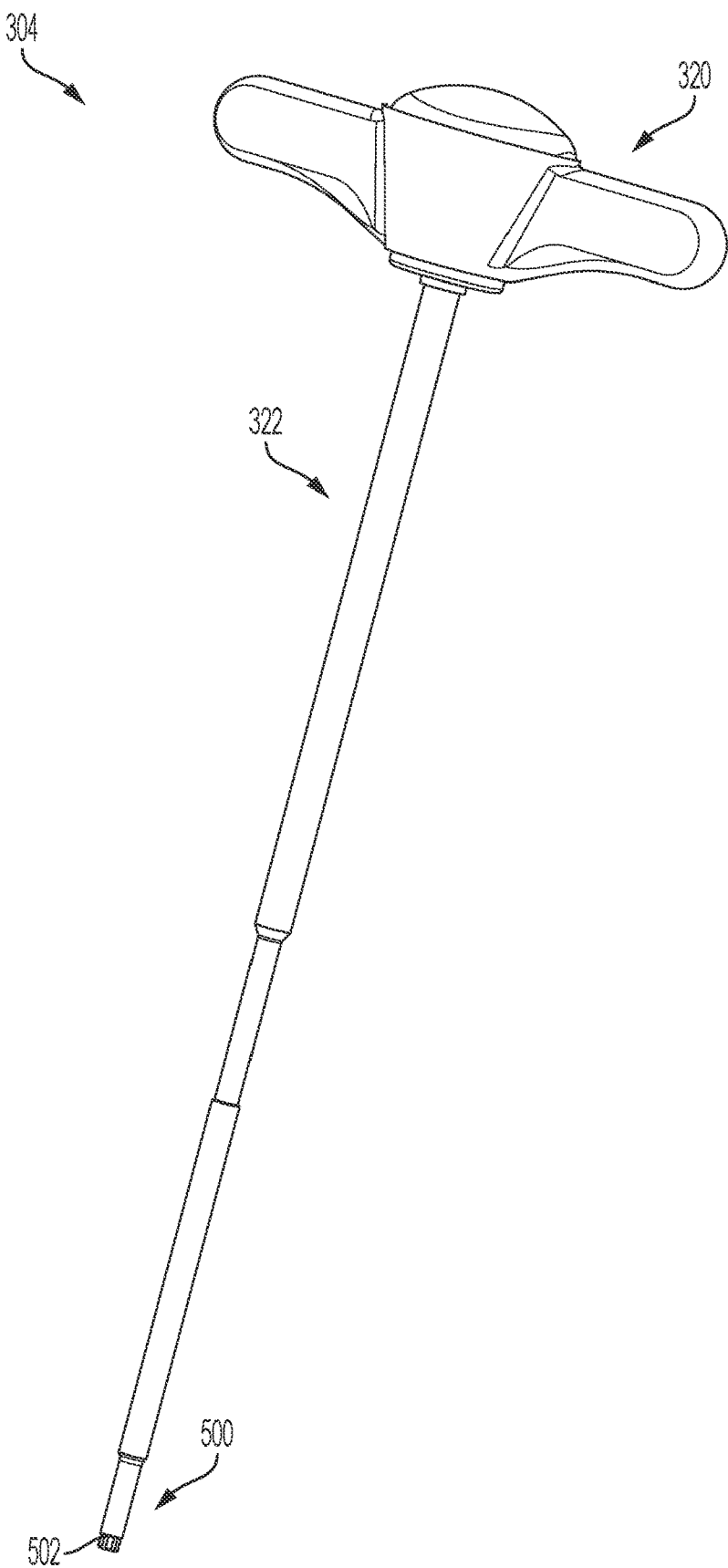
FIG. 5 is a perspective view of a driver of the surgical instrument shown in FIG. 3.

Referring now to FIGS. 3-5, there are provided illustrations of a surgical instrument 300 that combines a head positioner 302 and a driver 304 into a single integrated part, tool or instrument. The surgical instrument 104 of FIGS. 1-2 can be the same as or substantially similar to surgical instrument 300. As such, the discussion of surgical instrument 300 is sufficient for understanding surgical instrument 104 of FIGS. 1-2.

Figure 11:
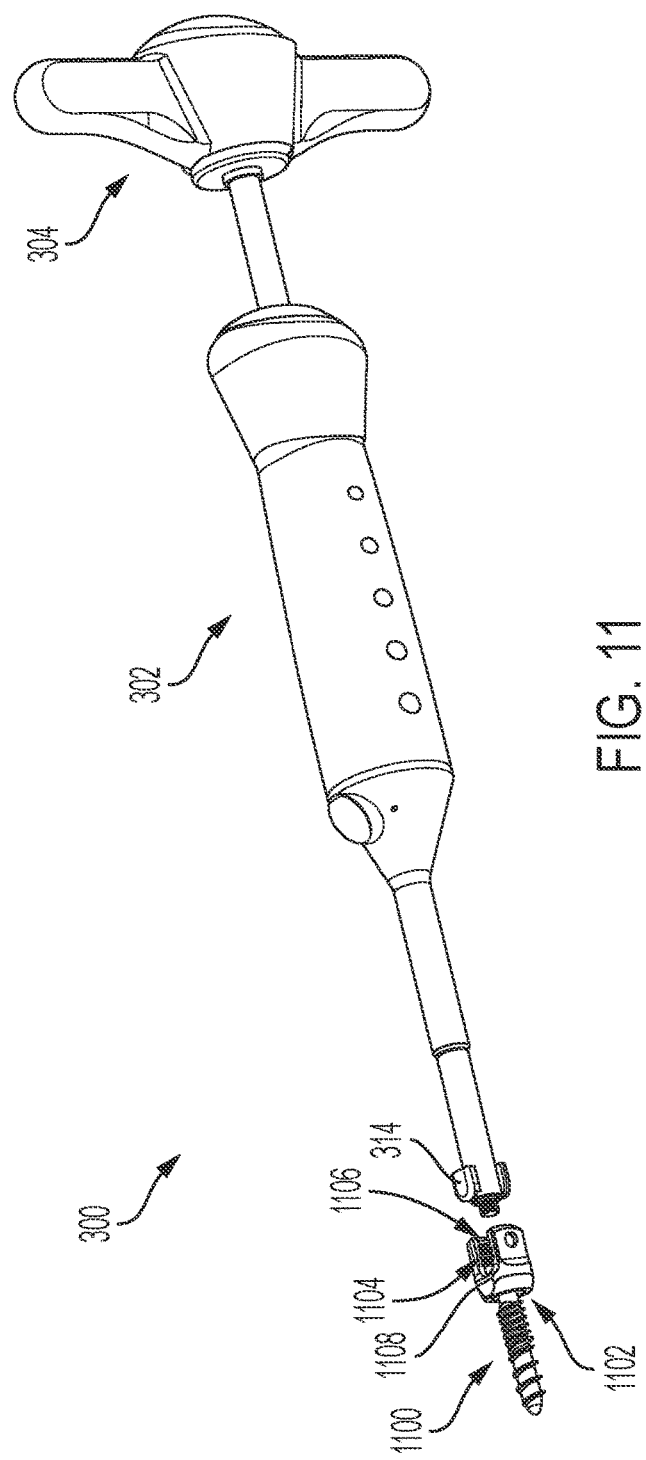
FIG. 11 provides a perspective view of an instrument being inserted into a receiver.
Figure 12:
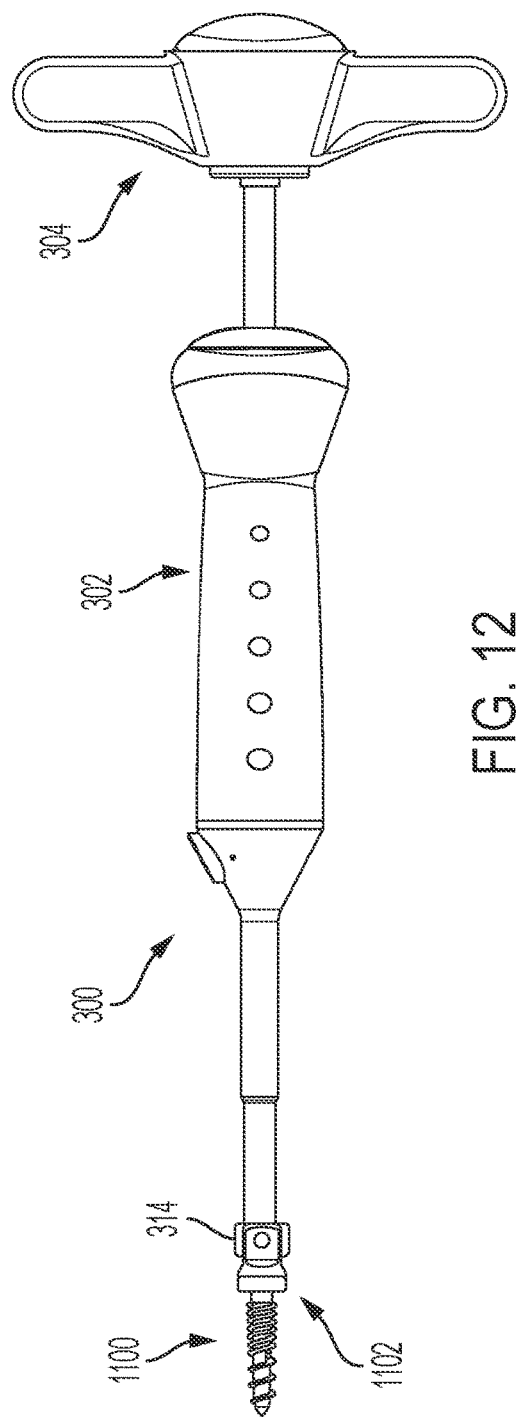
FIG. 12 provides a side view of an instrument engaging a receiver.
Figure 13:
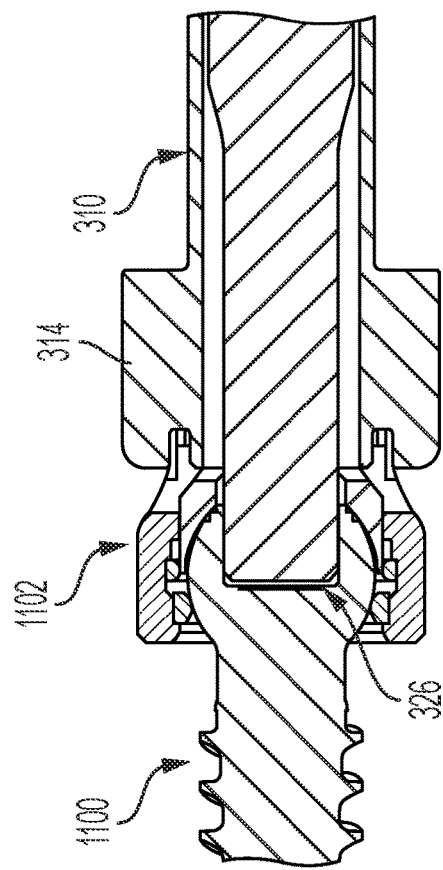
FIG. 13 provides a partial cross-sectional view showing an instrument engaging a screw and a receiver.
Figure 14:
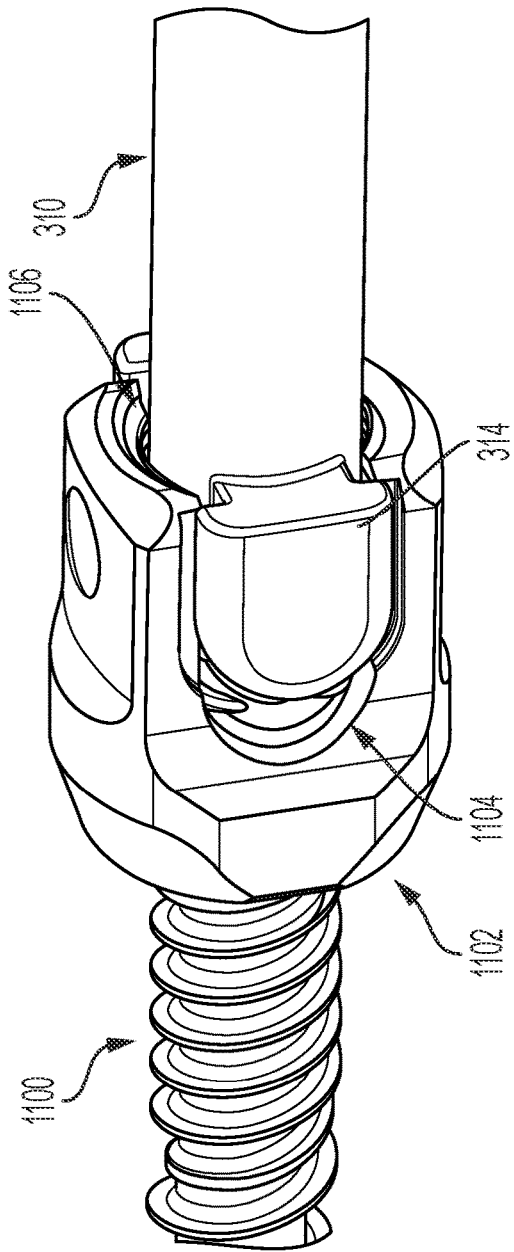
FIG. 14 provides a perspective view showing an instrument engaging a receiver.

The head positioner 302 is generally configured to facilitate proper orientation of a receiver (e.g., receiver 100 of FIG. 1 or 1102 of FIG. 11). The driver 304 is generally configured to advance a screw (e.g., screw 106 of FIG. 1 or 1100 of FIG. 11) in an object (e.g., during a medical procedure).

As shown in FIGS. 3-4, the head positioner 302 comprises a handle 306 and a shank 310. The handle 306 resides at a proximal end 352 of the shank 310. The shank 310 and handle 306 may be integrally formed as one part (not shown), or alternatively may be coupled to each other via a coupling means as shown in FIGS. 6-10. The coupling means can include, but is not limited to, a weld, an adhesive, and/or threads. The shank 310 and handle 306 are formed of stainless steel, titanium or other alloy which is resistant to corrosion. The handle 306 has a size and shape that allows an individual to easily grip and turn the same without discomfort. The handle 306 can be turned in two opposing directions shown by arrows 330, 332 of FIG. 3. Rotation of the handle 306 causes torque to be transferred from the individual to the shank 310.

Notably, the handle 306 has a head 324 formed at a distal end 312 thereof. The head 324 is configured to engage an inner surface of a receiver (e.g., receiver 100 of FIG. 1-2 or 1102 of FIGS. 11-14) so that rotation of the shank 310 is transferable to the receiver. In this regard, the head 324 is sized and shaped to be received in the socket (or u-shaped channel) of the receiver. The head 324 comprises at least one engagement structure 314 protruding outwardly therefrom. The engagement structure(s) 314 is(are) sized and shaped to facilitate rotation of the receiver. The present solution is not limited to the particular configuration of the head 324 shown in the drawings. The head 324 can have other shapes and sizes selected in accordance with a given application.

The shank 310 of the head positioner 302 is hollow. As such, the head positioner 302 comprises an elongate through hole or aperture 318 that extends from a proximal end 352 thereof to the distal end 312 thereof. The through hole/aperture 318 is sized and shaped to slidingly receive a portion of the driver 304, as well as limit an amount that the portion of the driver 304 can travel in a direction 340 within the head positioner 302. In this regard, the through hole/aperture 318 has a diameter or width that varies along its elongate length (as shown in FIGS. 6-9).

The driver 304 comprises a handle 320 and a shank 322. The shank 322 is inserted into the through hole/aperture 318 of the head positioner 302. The shank 322 is able to move linearly in two opposing directions (shown by arrows 340, 342 of FIG. 3) relative to the head positioner 302. This movement of the shank 322 is facilitated by the pulling of the handle 320 in direction 342 and the pushing of the handle in direction 340. The pulling/pushing of handle 320 causes the shank 322 to slide within the through hole/aperture 318 of the head positioner 302. The shank 322 is also able to freely rotate about a central axis 350 of the surgical instrument, while inserted within the head positioner 302.

The handle 320 resides at a proximal end 352 of the shank 322. The shank 322 and handle 320 may be integrally formed as one part (not shown), or alternatively may be coupled to each other via a coupling means as shown in FIGS. 6-10. The coupling means can include, but is not limited to, a weld, an adhesive, and/or threads. The shank 322 and handle 320 are formed of stainless steel, titanium or other alloy which is resistant to corrosion. The handle 320 has a size and shape that allows an individual to easily grip and turn the same without discomfort.

The handle 320 can be turned in two opposing directions shown by arrows 334, 336 of FIG. 3. Rotation of the handle 320 causes torque to be transferred from the individual to the shank 322.

A head 326 is provided at a distal end 312 of the shank 322. The head 326 is sized and shaped to be received in slot(s) of a screw (e.g., screw 106 of FIG. 1 or 1100 of FIG. 11), and facilitate an application of torque to the screw for driving the screw into an object (e.g., a bone 200 of FIG. 2, an implant or a receiver 100 of FIG. 1, 1102 of FIG. 11 during a medical procedure). In this regard, a torque may be applied to the driver 304 by an individual, whereby the head 326 is caused to rotate. The head 326 transfers the torque to the screw (e.g., screw 106 of FIG. 1), whereby the screw is caused to rotate such that the screw is advanced into or driven out of an object (e.g., a bone 200 of FIG. 2, an implant, or a receiver 100 of FIG. 1, 1104 of FIG. 11 during a medical procedure). The present solution is not limited to the particulars of this example.

Screws are well known in the art, and therefore will not be described herein. Any known or to be known screw can be used herein without limitation. The screws that are used with the surgical instrument 300 may be of the Phillip type having cross, hexalobe or star-shaped recesses in their heads. In this regard, the head 326 of the driver 304 has a tip that is sized and shaped to fit in the cross, hexalobe or star-shaped recesses of the screws.

Perspective views of an illustrative architecture for the tip 500 of the shank 322 is provided in FIGS. 3, 5 and 11. As shown in FIGS. 5 and 11, the tip 500 has a star-shape in which a plurality of protrusions 502 are provided for engaging recess sidewalls of the screws. This engagement between the tip 500 and a screw allows torque to be transferred from the set driver 304 to the screw.

Referring now to FIGS. 6-9, there are provided illustrations showing a plurality of different positions of the driver 304 relative to the head positioner 302. As noted above, the shank 322 of driver 304 is able to be received in and slide within the aperture 318 of the head positioner 302. The shank 322 of driver 304 has three shank portions 600, 602, 604 with different diameters. More specifically, shank portion 600 has a diameter that is greater than the diameters of shank portions 602 and 604. Shank portion 602 has a diameter that is greater than the diameter of shank portion 604. Shank portion 604 has a diameter that is less than the diameters of shank portions 600 and 602.

Figure 9:
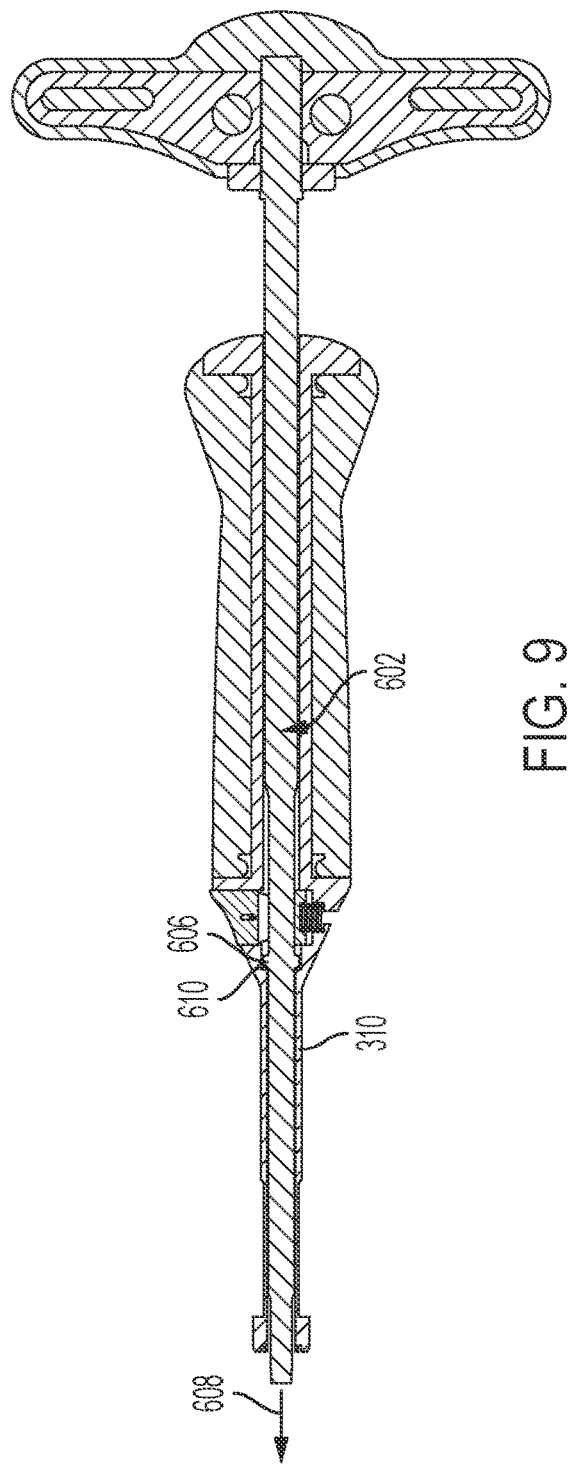
FIG. 9 provides an illustration showing the driver in a fourth position relative to the inline handle.
Figure 10:
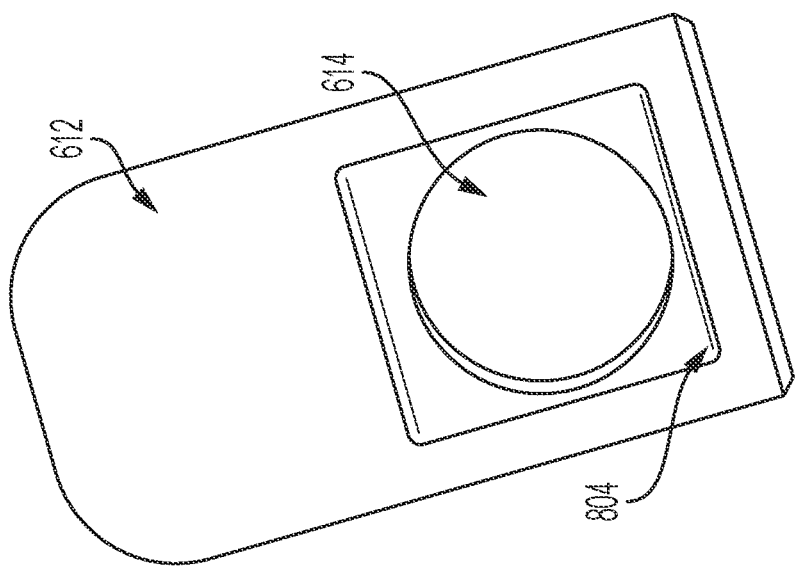
FIG. 10 provides an illustration that is useful for understanding operations of a button of the surgical instrument shown in FIGS. 1-9.

A flange 606 is formed on the shank portion 602 of the driver 304. The flange 606 is provided to facilitate limiting the distance in which the shank 322 can travel in direction 608 within/through the head positioner 302. The traveling distance of the shank 322 is limited via engagement of the flange 606 with an engagement surface 610 of the aperture 318 of the head positioner 302. This engagement is shown in FIG. 9. In FIG. 9, the flange 606 is abutting and in contact with the engagement surface 610 of the head positioner 302. The engagement surface 610 prevents the shank 322 of driver 304 from traveling further in direction 608 through the head positioner 302.

A coupler 308 is provided with the head positioner 302 and comprises an actuable structure to facilitate selective coupling and decoupling of the driver 304 to/from the head positioner 302. A cross-sectional view of the coupler 308 is provided in FIGS. 6-9. The coupler 308 comprises a rigid member 612 with an aperture 614 through which the shank 322 of the driver 304 can pass. A perspective view of the rigid member 612 is provided in FIG. 10.

The rigid member 612 is normally biased in a direction 800 by a resilient member 802. Illustrations showing the rigid member 612 in its normal/biased position are provided in FIGS. 8-9. The resilient member 802 can include, but is not limited to, a spring. The rigid member 612 can be transitioned from its normal biased position to a depressed/unbiased position. Illustrations showing the rigid member 612 in its depressed/unbiased position are provided in FIG. 6-7.

Figure 8:
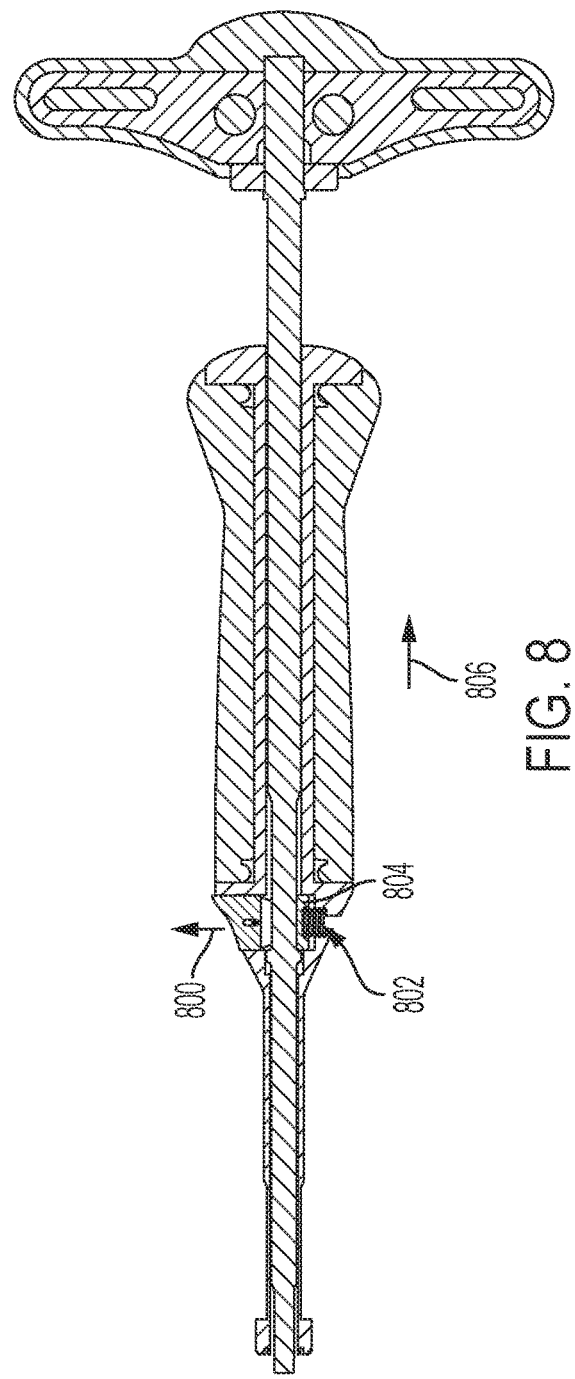
FIG. 8 provides an illustration showing the driver in a third position relative to the inline handle.

During operations, an individual actuates the coupler 308 via depression of the rigid member 612 thereof. Next, the individual inserts the shank 322 of the driver 304 into the aperture 318 of the head positioner 302. The individual then pushes the handle 320 of the driver 304 is a direction 608. In effect, the shank 322 of the driver 304 travels through the aperture 318 of the head positioner 302 and the aperture 614 of the coupler 308, as shown in FIGS. 6-7. The individual releases the coupler 308 when the flange 606 of the driver 304 no longer resides in the aperture 614 of the coupler 308, as shown in FIG. 8.

When the coupler is released, a portion 804 of the rigid member 612 is able to limit the distance in which the shank 322 of the driver 304 can travel in a direction 806. In this regard, portion 804 projects out and into the aperture 318 of the head positioner 302 when the coupler 308 is released, whereby the rigid member 612 obstructs at least a portion of the aperture 318 of the head positioner 302. Movement of the shank 322 in direction 806 is prevented when the flange 606 thereof engages the rigid member 612 as shown in FIG. 8.

The driver 304 can be decoupled from the head positioner 302 via actuation of the coupler 308 once again. When the coupler is actuated, the individual can pull the handle 320 of the driver 304 so as to cause the shank 322 to travel in direction 806 within the aperture 318 and out of the head positioner 302.

Figure 15:
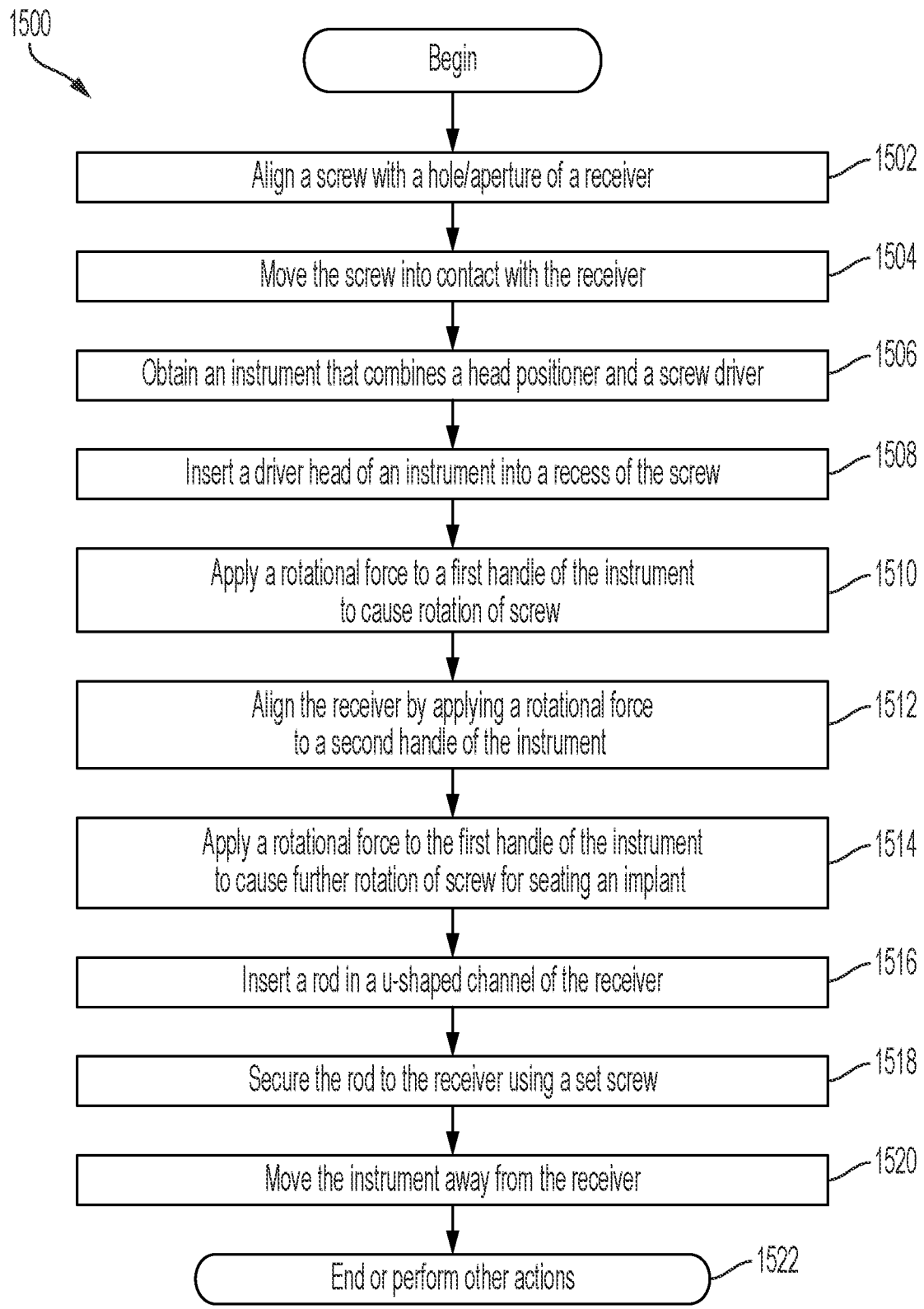
FIG. 15 provides a flow diagram of an illustrative medical procedure.

As noted above, the surgical instrument 300 can be used for medical procedures. A flow diagram of an illustrative medical procedure 1500 in which the surgical instrument 300 is employed is provided in FIG. 15. As shown in FIG. 15, the medical procedure 1500 involves (e.g., that shown in FIGS. 1-2), aligning a screw (e.g., screw 106 of FIG. 1 or screw 1100 of FIGS. 11-14) with a hole/aperture (e.g., hole/aperture 1106 of FIGS. 11-14) of a receiver (e.g., receiver 100 of FIG. 1 or 1102 of FIGS. 11-14), as shown by 1502. Thereafter, the screw is moved into contact with the receiver, as shown by 1504.

Once the screw is aligned and in contact with the receiver, an individual obtains a surgical instrument 300, as shown by 1506. The surgical instrument 300 combines a head positioner and a screw driver into a single integrated part, tool or instrument. In 1508, the individual inserts the distal end 312 of the surgical instrument 300 into the receiver until the driver's head 326 resides in a cross, hexalobe or star-shaped recess of the screw. The individual then applies a rotational force in 1510 to a first handle 320 of the surgical instrument 300 for seating an implant.

This rotational force is applied by rotating the first handle 320 in a clockwise direction (e.g., direction 334 of FIG. 3) or alternatively in a counter clockwise direction (e.g., direction 336 of FIG. 3). This rotational force or torque is transferred from the first handle 320 to the screw via shank 322 of the surgical instrument 300, and causes a threaded portion of the screw to threadingly engage an object (e.g., a spinal bone 200 of FIG. 2).

In some scenarios, the rotation of the screw is continued so that the screw is tightened, whereby the receiver is securely coupled to the object. At this time, a rod (e.g., rod 108 of FIG. 1) can be inserted into the u-shaped channel (e.g., channel 102 of FIG. 1 or 1104 of FIGS. 11-14) of the receiver. The rod is secured to the receiver via a set screw (e.g., set screw 110 of FIG. 1) which may be tightened via surgical instrument 300 or another surgical instrument.

In other scenarios, the surgical instrument 300 is further used to properly align the receiver with at least one other receiver or the orientation of a rod or connecting element to be placed in the receiver or bent at various angles, which is also coupled to the object, prior to when the screw is tightened. Accordingly, the medical procedure 1500 can continue with 1512.

In 1512, a rotational force is applied to a second handle 306 of the surgical instrument 300. This rotational force is applied by rotating the second handle 306 in a clockwise direction (e.g., direction 330 of FIG. 3) or alternatively in a counter clockwise direction (e.g., direction 332 of FIG. 3). This rotational force or torque is transferred from the second handle 306 to the receiver via shank 310 of the surgical instrument 300, and causes an orientation of the receiver's u-shaped channel to change relative to the object and/or other receiver(s).

Once the receiver is aligned, a rotational force is once again applied to the first handle 320 of the surgical instrument 300, as shown by 1514. This rotational force causes the screw to rotate and further advance into the object (e.g., for seating an implant).

In 1516, a rod (e.g., rod 108 of FIG. 1) is at least partially inserted through the u-shaped channel (e.g., u-shaped channel 102 of FIG. 1 or 1104 of FIGS. 11-14) formed between sidewalls (e.g., sidewalls 1108 of FIGS. 11-14) of the receiver. Next in 1518, a set screw (e.g., set screw 110 of FIG. 1) is used to secure the rod to the receiver. 1518 involves: aligning the set screw with the threaded hole/aperture (e.g., hole/aperture 1106 of FIGS. 11-14) of the receiver; causing the set screw to come in contact with the receiver; and using a surgical instrument to cause rotation of the set screw such that the set screw threadingly engages the receiver. The surgical instrument used in 1518 to rotate the set screw can include, but is not limited to, surgical instrument 300 of the present solution and/or a set screw reducer.

During rotation of the set screw, the set screw applies a pushing force directly to the rod as it is being advanced through the threaded hole of the receiver. This pushing force causes the rod to move in a direction towards the object. The set screw is then tightened against the rod to prevent the rod from moving relative to the object. The set screw can exert a compression or clamping force to the rod. In this way, the rod is securely retained in a given position relative to the object by the set screw and the receiver.

Next in 1520, the surgical instrument 300 is moved away from the receiver. In some scenarios, the surgical instrument 300 may need to be repaired, cleaned or otherwise disinfected. Accordingly, other operations may be performed in 1522. These other operations can include, but are not limited to, disassembling the surgical instrument 300. The manner in which the surgical instrument 300 can be disassembled will become evident as the discussion progresses.

Figure 16:
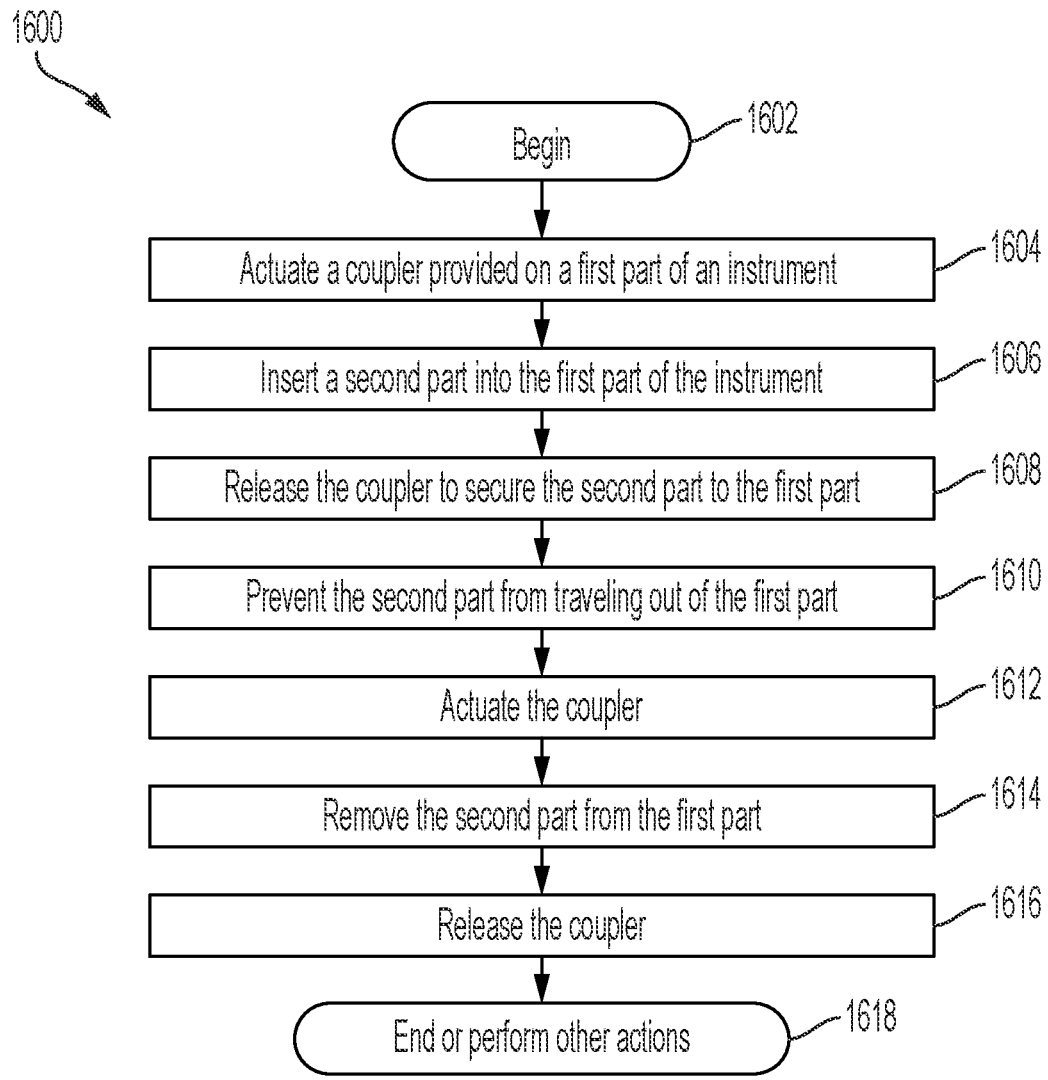
FIG. 16 provides an illustrative method for operating a surgical instrument.

Referring now to FIG. 16, there is provided an illustrative method 1600 for operating a surgical instrument (e.g., surgical instrument 300 of FIG. 3). Method 1600 begins with 1602 and continues with 1604 where a coupler (e.g., coupler 308 of FIG. 3) of the surgical instrument is actuated. The coupler is provided on a first part (e.g., head positioner 302 of FIG. 3) of the surgical instrument. In 1606, a second part (e.g., driver 304 of FIG. 3) is inserted into the first part of the surgical instrument while the coupler is being actuated (e.g., depressed). The coupler is released in 1608 when the second part is fully inserted into the first part of the surgical instrument. In 1610, the second part is prevented by the coupler from traveling out of the first part.

At some later time, the coupler of the surgical instrument is once again actuated (e.g., depressed) in 1612. The second part can now be removed from the first part of the surgical instrument, as shown by 1614. The coupler is released in 1616, i.e., when the second part is no longer inserted into the first part. Subsequently, 1618 is performed where method 1600 ends or other actions are performed (e.g., return to 1602 for repairing the surgical instrument using a replacement second part, or reassembling the surgical instrument using the same second part).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for performing a medical procedure, comprising:

obtaining a surgical instrument that combines a head positioner and a driver into a single integrated tool, the driver being at least partially inserted through an elongate aperture formed in the head positioner so as to extend from a proximal end of the head positioner to a distal end of the head positioner;

actuating an actuable structure of the head positioner;

sliding the driver within the elongate aperture formed in the head positioner in a first direction towards a distal end of the surgical instrument until a flange extending out and away from a shank portion of the driver travels through the actuable structure;

releasing the actuable structure of the head positioner to capture the flange in a closed space provided between an internal inward projecting sidewall of the head positioner and the actuable structure;

allowing the flange to slide within the closed space and engage the internal inward projecting sidewall;

using the flange and the internal inward projecting sidewall of the head positioner to limit an amount that the driver can linearly travel in the first direction within the elongate aperture formed in the head positioner;

using the flange and the actuable structure of the head positioner to limit an amount that the driver can linearly travel in a second direction within the elongate aperture formed in the head positioner;

causing a screw to threadingly engage an object via rotation of the driver around a central axis of the surgical instrument; and changing an orientation of a receiver via rotation of the head positioner about a portion of the driver.

2. The method according to claim 1, further comprising causing the screw to advance into the object by further rotating the driver about the central axis of the surgical instrument.

3. The method according to claim 1, further comprising actuating the actuable structure of the head positioner to stop limiting the amount that the driver can linearly travel in the second direction within the elongate aperture formed in the head positioner.

4. The method according to claim 1, wherein the actuable structure comprises a button.

5. The method according to claim 3, further comprising removing the driver from the elongate aperture formed in the head positioner.

6. The method according to claim 5, further comprising discontinuing actuation of the actuable structure when the driver is at least partially removed from the elongate aperture formed in the head positioner.

7. The method according to claim 1, wherein the actuable structure is resiliently biased by a resilient member into a first position in which the actuable structure at least partially obstructs the elongate aperture formed in the head positioner.

8. The method according to claim 7, further comprising actuating the actuable structure so that the resilient member no longer causes the actuable structure to obstruct the elongate aperture formed in the head positioner.

9. The method according to claim 8, further comprising releasing the actuable structure so that the resilient member once again causes the actuable structure to obstruct the elongate aperture formed in the head positioner.

10. A surgical instrument, comprising:

a single integrated tool comprising both a head positioner and a driver, the driver being at least partially inserted through an elongate aperture formed in the head positioner so as to extend from a proximal end of the head positioner to a distal end of the head positioner; and an actuable structure coupled to the head positioner;

wherein the driver is configured to transfer torque to a screw, the driver comprising a shank that is linearly and rotationally movable within the elongate aperture of the head positioner, and that has a distal end with a head sized and shaped to fit in a socket of the screw;

wherein, when the actuable structure is actuated, the driver can be slide within the elongate aperture formed in the head positioner in a first direction towards a distal end of the surgical instrument until a flange extending out and away from the shank of the driver travels through the actuable structure;

wherein, when the actuable structure is released, the flange is captured in a closed space formed in the elongate aperture between the internal inward projecting sidewall of the head positioner and the actuable structure; and wherein the flange is movable within the closed space and engageable with the internal inward projecting sidewall, an amount by which the flange can linearly travel in a first direction within the closed space is limited by the internal inward projecting sidewall of the head position, and an amount by which the flange can linearly travel in the second direction within the closed space is limited by the actuable structure.

11. The surgical instrument according to claim 10, wherein actuation of the actuable structure causes the actuable structure to stop limiting the amount that the driver can linearly travel in the second direction.

12. The surgical instrument according to claim 10, wherein the actuable structure comprises a button.

13. The surgical instrument according to claim 10, wherein the driver is removable from the elongate aperture of the head positioner when the actuable structure is actuated.

14. The surgical instrument according to claim 10, wherein the actuable structure comprises a rigid member that is resiliently biased by a resilient member into a first position in which the rigid member at least partially obstructs the elongate aperture of the head positioner.

15. The surgical instrument according to claim 14, wherein the rigid member comprises a hole through which the shank of the driver passes when the driver is inserted into the head positioner.

16. The surgical instrument according to claim 14, wherein the resilient member no longer causes the actuable structure to obstruct the elongate aperture formed in the head positioner when the actuable structure is depressed.

17. The surgical instrument according to claim 10, wherein the head of the driver extends through and projects out of a distal end of the head positioner.

* * * * *